United States Patent [19]
Bond et al.

[11] Patent Number: 5,504,256
[45] Date of Patent: Apr. 2, 1996

[54] CATALYTIC PRODUCTION OF ARYL ALKYL HYDROPEROXIDES BY POLYNUCLEAR TRANSITION METAL AGGREGATES (LAW229)

[75] Inventors: Jeffrey E. Bond, Flemington; Sergiu M. Gorun, Little Falls; George W. Schriver, Somerville; Robert T. Stibrany, Long Valley; Thomas H. Vanderspurt, Stockton, all of N.J.

[73] Assignee: Exxon Research and Engineering Company, Florham Park, N.J.

[21] Appl. No.: 402,077

[22] Filed: Mar. 10, 1995

[51] Int. Cl.$^6$ .................. C07C 409/08; C07C 409/10
[52] U.S. Cl. .............. 568/575; 568/569; 568/573; 568/574
[58] Field of Search .................... 568/574, 575, 568/569, 573

[56] References Cited

U.S. PATENT DOCUMENTS 4,013,725  3/1977  Yonemitsu et al. .............. 568/574
5,025,101  6/1991  Gorun et al. .................... 556/50
5,196,598  3/1993  Iwane et al. .................... 568/575

OTHER PUBLICATIONS

Christou, G., *Acc. Chem. Res.*, 22, pp. 328–335 (1989).
Wieghardt, K., *Angew Chem. Int. Ed. Engl.*, 28, 1153–1172, (1989).
Vincent, J., et al., *Advances in Organic Chemistry*, vol. 33, pp. 197–256 1989.
Lippard, S. J., *Progress in Organic Chemistry*, vol. 37, pp. 99–142 (1989).

*Primary Examiner*—Werren B. Lone
*Attorney, Agent, or Firm*—Joseph J. Dvorak

[57] ABSTRACT

A method is provided for preparing organic hydroperoxides by oxidizing aryl alkyl hydrocarbons having a benzylic hydrogen with an oxygen containing gas using as a catalyst an oxo (hydroxo) bridged tetranuclear metal complex having a mixed metal core, one metal of the core being a divalent metal selected from Zn, Cu Fe, Co, Ni, Mn or mixtures thereof and another metal being a trivalent metal selected from In, Fe, Mn, Ga, and Al.

8 Claims, 2 Drawing Sheets

CATALYTIC PRODUCTION OF ARYL ALKYL HYDROPEROXIDES BY POLYNUCLEAR TRANSITION METAL AGGREGATES (LAW229)

FIELD OF THE INVENTION

This invention relates to a process for preparing organic hydroperoxides by oxidizing aryl alkyl hydrocarbons in the presence of an oxygen-containing gas and certain polynuclear transition metal complexes as catalysts.

BACKGROUND OF THE INVENTION

The production of organic hydroperoxides from aryl alkyl hydrocarbons in the presence of various transition metal salt complexes has been described in the literature. See, for example, U.S. Pat. No. 2,954,405 disclosing the production of organic hydroperoxides by autooxidation of hydrocarbons in the presence of molecular oxygen and metal phthalocyanines as catalysts. Similarly, U.S. Pat. No. 4,013,725 discloses a process for preparing hydroperoxides in a homogeneous system by autooxidizing secondary alkyl group-substituted methylbenzenes in the presence of water, a base, an oxygen containing gas, and a water-soluble chelate compound in which multidentate ligands are coordinated to at least one metal from the class of cobalt, nickel, manganese, copper, and iron.

In U.S. Pat. No. 5,025,101 and U.S. Pat. No. 5,183,945 tetranuclear manganese complexes, and their method of preparation, and their use as catalyst in the production of hydroperoxide are disclosed.

More recently, in copending U.S. Ser. No. 402,070 there is disclosed a new class of tetranuclear metal complexes having a mixed metal core. The present invention is predicated on the discovery that certain of those tetranuclear, mixed metal complexes are useful as catalysts in producing organic hydroperoxides.

SUMMARY OF THE INVENTION

Accordingly, this invention provides a method for preparing organic hydroperoxides, comprising contacting an aryl alkyl hydrocarbon having a benzylic hydrogen with an oxygen containing gas in the presence of an oxo (hydroxo) bridged tetranuclear metal complex having a mixed metal core, one metal of the core being a divalent metal selected from Zn, Cu, Fe, Co, Ni, Mn or mixtures thereof and another metal being a trivalent metal selected from In, Fe, Mn, Ga, and Al.

DETAILED DESCRIPTION OF THE INVENTION

Figure 1:
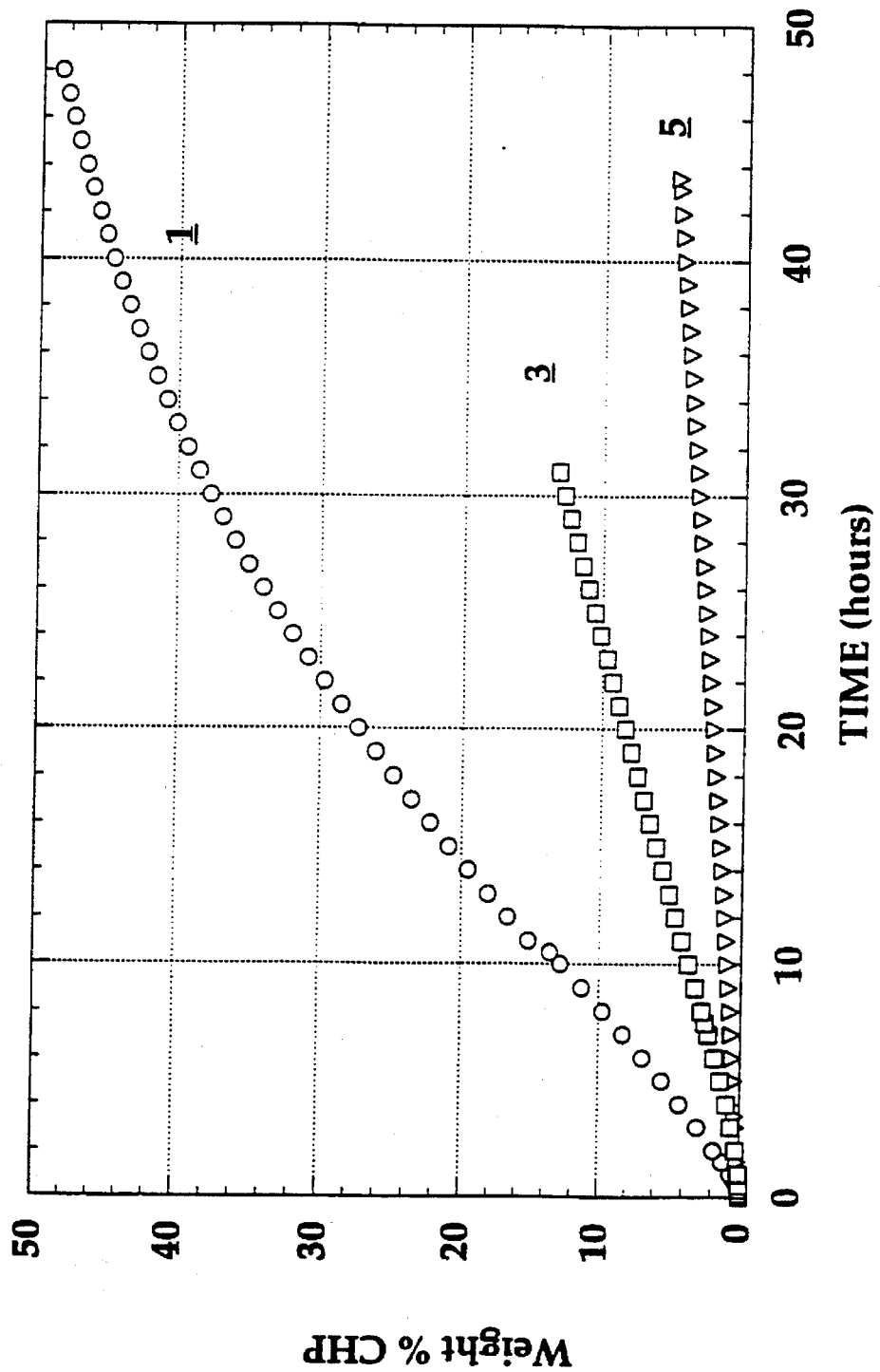
FIGS. 1 and 2 show the weight percent of cumene hydroperoxide produced from cumene in the presence of and various catalysts by the process of the present invention. Also shown in FIG. 2 is the amount of cumene hydroperoxide produced in the presence of cumene, air and cumene hydroperoxide as an initiator.

The process of the present invention is carried out by contacting an aryl alkyl hydrocarbon with an oxygen-containing gas and a catalytically effective amount of oxo (hydroxo) bridged tetranuclear metal complex having a mixed metal core.

The aryl alkyl hydrocarbons employed as starting materials in this process may be obtained from commercial sources. Preferably the aryl alkyl hydrocarbons will have a melting point within the range of temperatures at which the process of the present invention is operated or be capable of being solubilized in an inert solvent. Importantly, the aryl alkyl hydrocarbons should contain a benzylic hydrogen. An example of useful aryl alkyl hydrocarbons is represented by the general formula:

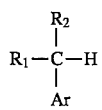

where $R_1$ and $R_2$ may be the same or different organo groups, preferably alkyl groups having from 1 to about 10 carbon atoms, or hydrogen and Ar is an aromatic or substituted aromatic group, such as alkyl and halo, substitute aromatic groups. In the case of alkyl substituted aromatic groups, the alkyl group generally will have from 1 to about 10 carbon atoms.

The oxygen containing gas used preferably is air or oxygen, and, more preferably, is air. The tetranuclear metal complexes used as catalysts in the process of this invention have the general formula:

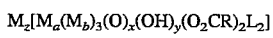

wherein M is ammonium, an alkali metal ion or an alkaline earth metal ion; z is 4 when M is ammonium or alkali metal ion and 2 when M is an alkaline earth metal ion; $M_a$ is a divalent metal or mixture of divalent metals; $M_b$ is trivalent metal or mixture of trivalent metals; x and y are numerical values the sum of which equals 2; R is hydrogen or a hydrocarbyl group; and L is a ligand having the formula:

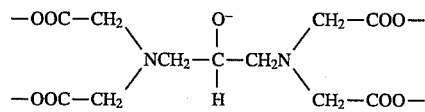

Preferably M is Mg, Ca, Sr, Ba or mixtures thereof; $M_a$ is Zn, Cu, Fe, Co, Ni, Mn or mixtures thereof, and $M_b$ is In, Fe, Mn, Ga, Al or mixtures thereof. Also, when R is a hydrocarbyl group, preferably it will have from 1 to about 30 carbon atoms and, more preferably, is an alkyl group having from 1 to about 10 carbon atoms. When R is an aralkyl group, it preferably will have from 7 to about 10 carbon atoms.

The catalysts used in the method of the present invention may be prepared as follows.

The compounds of the present invention are prepared by forming an aqueous solution containing: (a) a compound (Compound I) having the formula:

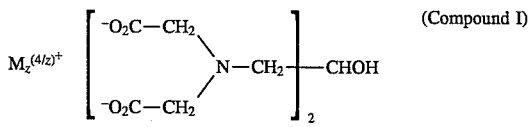

(Compound I)

wherein M is ammonium, alkaline, or an alkaline earth metal ion; z is 4 when M is alkali metal or ammonium ion and 2 when M is an alkaline earth metal ion, (b) a mixture of a water soluble salt of at least one divalent metal $M_a$ and a trivalent metal $M_b$; and (c) a source of a carboxylate, $RCO_2$—, where R is hydrogen or a hydrocarbyl group whereby a compound having the formula $M_z[M_a(M_b)_3(O)_x(OH)_y(O_2CR)L_2]$ is prepared.

Exemplary salts of $M_a$ and $M_b$ suitable for use in the present invention include metal chlorides, bromides, nitrates, tetrafluoroborates, and sulfates, provided however, that sulfates are not used when M is Ca, Ba or Sr.

Exemplary sources of carboxylate include carboxylic acids and alkaline metal salts of carboxylic acids.

Among suitable aqueous containing solutions are water, water-alcohol and water-dimethyl formamide mixtures. In general, it is particularly preferred to use water as the solvent.

The molar ratio of Compound I to the metal salts containing $M_a$ and $M_b$ generally will be in the range of from about 1:1 to about 1:3 and preferably about 1:2.

Because the acid analog of the ligand L is commercially available, it is particularly preferred in the practice of the present invention to prepare an aqueous containing solution of Compound I by first neutralizing an aqueous solution of its conjugated acid with an alkali or alkaline earth metal hydroxide or mixture thereof, and thereafter adding the metal carboxylates or metal salts and source of carboxylate.

In one embodiment, the solution is formed in situ by adding an oxidant, such as air, oxygen or hydrogen peroxide to an aqueous solution of Compound I, a carboxylate source and (i) a water soluble salt of a divalent metal $M_a$ and a metal oxidizable to a trivalent metal, $M_b$; or (ii) a water soluble salt of a divalent metal oxidizable to a trivalent metal, $M_b$, the addition being in an amount and for a time sufficient to oxidize at least part of the oxidizable divalent metal to the trivalent metal $M_b$.

As pointed out above, this aqueous mixture is then oxidized if needed. The need for oxidation arises only when $M_b$ is not present in its trivalent state to start with. As shown later in Preparations 11 and 12, for the preparation of the complex in which $M_a$ is Mn and $M_b$ is Ga, there is no need for oxidation because Ga is already present as Ga(III). On the other hand, as shown in Preparations 8, 9 and 10 for the preparation of the complex in which $M_a$ is Zn and $M_b$ is Mn, one may start with Mn(II) salts and oxidize the Mn(II) to the required Mn(III) state. This is achieved by adding an oxidant such as air, molecular oxygen, or hydrogen peroxide. When air or oxygen is employed, the gas is bubbled through the mixture at temperatures in the range of about 20° C. to about 60° C. and in an amount sufficient to form the desired compound. When hydrogen peroxide is used as the oxidant, in general the peroxide will have a concentration range of about 10 wt. % to 30 wt. % and, preferably, about 25 wt. % and will be used in excess, for example, up to about 10 times the stoichiometric amount required. The addition of hydrogen peroxide to the reaction mixture results in an exothermic reaction and consequently it is particularly preferred to maintain the temperature of the reaction mixture during oxidation in the range of about 10° C. to 60° C., and preferably, in the range of about 20° C. to 40° C.

The amount of catalyst used will vary depending upon the nature and amount of the organic starting material to be oxidized. In general from about 0.001 to about 0.5 parts by weight of catalyst per 100 parts of substrate and preferably from about 0.1 to about 0.2 parts per 100 parts of substrate are satisfactory.

In the process of the present invention, the solvent for the reaction is preferably an excess amount of the aryl alkyl hydrocarbon to be oxidized; however, hydrocarbons such as benzene, chlorobenzene, halogenated hydrocarbons, and the like may be employed as solvents.

Preferably the hydrocarbon, catalyst and oxygen or oxygen containing gas are contacted in such a way as to provide for good mixing, such as rapid bubbling of the gas through the mixture or mechanical agitation.

Preferably air is used in the contacting.

The flow rate of air is not critical and the optimum rate will vary depending on the reaction temperature and pressure employed. In the case of the oxidation of cumene to cumene hydroperoxide, for example, the flow rate of air preferably will be at least 2 liters/hr up to about 10 liters/hr per 100 g of cumene.

The reaction temperature may range from about 0° C. to about 90° C., preferably from about 60° C. to about 80° C. Temperatures at the lower end of the preferred range are more desirable.

Typically the contacting is conducted at atmospheric pressure. Importantly, the present invention results in the selective oxygenation of the aryl alkyl hydrocarbon and does not oxygenate the aromatic or aliphatic hydrocarbons present in the starting material. The method also does not require the presence of an initiator as is the case in other processes. Indeed, the catalyzed method of the present invention has a reaction rate that is greater than the process that uses cumene hydroperoxide as an initiator.

In conducting the method of this invention, the formation of the corresponding organic hydroperoxide can be monitored, for example, by analyzing aliquots by NMR, iodometric titration, chromatography or other means readily known to one skilled in the art. Also, the organic hydroperoxide is readily recovered from the reaction mixture by conventional methods, for example distillation, and as a result, the process may be run in batch or continuously. In a continuous process, the aryl alkyl hydrocarbon starting material may be passed over the catalyst in a bed or otherwise contacted with the catalyst. The organic hydroperoxide may be withdrawn and the organic starting material recycled.

EXAMPLES

A. Catalyst Preparation

A series of detailed catalyst preparations are provided herein to illustrate the general preparation techniques previously described. In the preparations which follow, DHPTA refers to 1,3-diamino-2-hydroxypropane-N,N,N'N'-tetraacetic acid; DMF is dimethylformamide; MeOH is methyl alcohol. Also, in those preparations in which the subscript s is used in the formula, s is a value greater than zero but less than 1, depending upon the ratio of mixed divalent metals used.

Preparation 1

Preparation of $Ba_2[(Cu_{0.4}Mn_{0.6})Mn_3(O)(OH)(O_2CCH_3)_2L_2]$

In a 50 ml Erlenmeyer flask, 268 mg of DHPTA was added to ~7 ml $H_2O$. Then enough $Ba(OH)_2 \cdot H_2O$ was added to give a clear solution, followed by 93 mg of $Cu(O_2CCH_3)_2 \cdot H_2O$ and 343 mg of $Mn(O_2CCH_3)_2 \cdot 4H_2O$. About ½ ml of MeOH and ~1 ml of DMF was added next, while stirring. After the pH was brought to ~8 by adding slowly $Ba(OH)_2$, the solution was treated with ~1 ml of ~25% $H_2O_2$. During this addition, the solution color changed from blue to brown. This filtered solution gave crystals by evaporation. The structure of the product was determined by simple crystal x-ray diffraction and sorption spectroscopy. The simple crystal x-ray analysis revealed the presence of Cu(II) ions which selectively replaced the Mn(II) ions.

Preparation 2

Preparation of $Ca_2[(Cu_sMn_{1-s})Mn_3(O)(OH)(O_2CCH_3)_2L_2]$

The procedure of Preparation 1 was followed except that $Ca(OH)_2$ was used in place of $Ba(OH)_2$.

Preparation 3

Preparation of $Ba_2[CuFe_3(O)(OH)(O_2CCH_3)_2L_2]$

In a 50 ml Erlenmeyer flask, 268 mg of DHPTA and 100 μl of 100% $CH_3COOH$ was added to ~8 ml $H_2O$. The pH was brought to ~6 with $Ba(OH)_2.H_2O$. Then 110 mg of $Cu(O_2CCH_3)_2.4H_2O$ and 345 mg of $Fe(NO_3)_3.6H_2O$ was added to the solution. Then the pH was brought to ~7.5 with $Ba(OH)_2.H_2O$ and 1 ml DMF was added. The yellow green solution was filtered and the product crystallized by evaporation.

Preparation 4

Alternate Preparation of $Ba_2[CuFe_3(O)(OH)(O_2CCH_3)_2L_2]$

In a 50 ml Erlenmeyer flask, 268 mg of DHPTA was added to 10 ml $H_2O$. The solution was brought to pH ~6 with $Ba(OH)_2.H_2O$. Then 105 mg of $Cu(O_2CCH_3)_2.4H_2O$ and 540 mg of $Fe(ClO_4)_3.6H_2O$ and 100 μl of $CH_3COOH$ were all added. After stirring, the pH was brought to 7.5–8.0 with $Ba(OH)_2$ and 1 ml DMF was added. The crystalline product was obtained by evaporation.

Preparation 5

Preparation of $Ca_2[ZnGa_3(O)(OH)(O_2CCH_3)_2L_2]$ 268 mg of DHPTA was added to about 8 ml $H_2O$ then brought to pH 6 using $Ca(OH)_2$. Then 115 mg of $Zn(O_2CCH_3).2H_2O$ and 320 mg of $Ga(NO_3)_3.6H_2O$ and 100 μl glacial acetic acid was added to the solution. The pH was then brought to about 8 with $Ca(OH)_2$ and 2 ml of DMF was added. The solution was filtered and the product was obtained by crystallization.

Preparation 6

Preparation of $Ba_2[ZnGa_3(O)(OH)(O_2CCH_3)_2L_2]$

In a 50 ml Erlenmeyer flask, 268 mg of DHPTA was added to ~8 ml $H_2O$. The solution was brought to pH 6 with $Ba(OH)_2.H_2O$. Then 120 mg of $Zn(O_2CCH_3)_2.2H_2O$ and 330 mg of $Ga(NO_3)_3.6H_2O$ was added while stirring. The pH was brought to 7.5 with $Ba(OH)_2.H_2O$. Following the addition of 1 ml of DMF, the solution was filtered and the product crystallized by evaporation.

Preparation 7

Preparation of $Na_4[ZnGa_3(O)(OH)(O_2CCH_3)_2L_2]$

In a 50 ml Erlenmeyer flask 268 mg of DHPTA was added to ~6 ml $H_2O$. The solution was brought to pH ~6.0 with NaOH. Then three drops of 100% $CH_3COOH$ was added, followed by 105 mg $Zn(O_2CCH_3)_2.2H_2O$ and 340 mg of $Ga(NO_3)_3.6H_2O$. The pH was then brought to ~8 using NaOH, the solution was filtered and 1 ml DMF added. The product was obtained by crystallization.

Preparation 8

Preparation of $Ca_2[(Zn_sMn_{1-s})Mn_3(O)(OH)(O_2CCH_3)_2L_2]$ 268 mg of DHPTA was added with 10 ml $H_2O$ to a 50 ml flask. The solution was brought to pH 8 with powderd $Ca(OH)_2$. In another flask, 330 mg of $Mn(O_2CCH_3)_2.4H_2O$ and 105 mg $Zn(O_2CCH_3)_2.2H_2O$ was dissolved in 10 ml of 1:1 $H_2O$:MeOH. Then 200 mg of $CaCl_2$ was also dissolved in the $(Zn,Mn)(O_2CCH_3)_2$ solution. Next, the Mn/Zn containing solution was added to the DHPTA solution and stirred for 5 minutes. The pH was adjusted to 8.0 with $Ca(OH)_2$, after which ½ ml of 30% $H_2O_2$ was added dropwise. Finally, 4 ml of DMF was added, the solution was filtered and the product was obtained by crystallization.

Preparation 9

Alternative preparation of $Ca_2[(Zn_sMn_{1-s})Mn_3(O)(OH)(O_2CCH_3)_2L_2]$

In a 50 ml Erlenmeyer flask 268 mg of DHPTA was added to ~7 ml $H_2O$. The solution was brought to pH ~6.5 with $Ca(OH)_2$. Then 105 mg at $Zn(O_2CCH_3)_2.2H_2O$ and 330 mg of $Mn(O_2CCH_3)_2.6H_2O$ was added to the solution. The pH was brought to ~8 with $Ca(OH)_2$ and 0.5 ml of ~30% $H_2O_2$ was added giving off heat and gas. 1 ml of DMF was then added. The crystalline product was obtained by evaporation.

Preparation 10

Preparation of $Ba_2[(Zn_sMn_{1-s})Mn_3(O)(OH)(O_2CCH_3)_2L_2]$

In a 50 ml Erlenmeyer flask containing 5 ml $H_2O$, 100 mg of $Ba(OH)_2.H_2O$ was neutralized with concentrated HCl to pH 7. Then 330 mg of $Mn(O_2CCH_3)_2.4H_2O$ and 105 mg $Zn(O_2CCH_3)_2.2H_2O$ were added, along with 10 ml of 1:1 $H_2O$/MeOH. In another 50 ml flask, 268 mg of DHPTA was added to 10 ml of $H_2O$. This was neutralized with solid $Ba(OH)_2$ while stirring. The two solutions were mixed together and stirred for about 10 minutes, after which the pH was adjusted to 8.0 with solid $Ba(OH)_2.H_2O$. Next, 0.5 ml of 30% $H_2O_2$ was added dropwise. Then 5 ml of DMF was added, the solution was stirred 10 minutes and filtered. The product was obtained by crystallization.

Preparation 11

Preparation of $Na_4[MnGa_3(O)(OH)(O_2CCH_3)_2L_2]$

In a 50 ml Erlenmeyer flask, 268 mg of DHPTA was added to ~8 ml $H_2O$ under an Ar blanket. The pH was brought to ~6 with NaOH. Then 100 μl of 100% $CH_3COOH$ was added, followed by 110 mg of $Mn(O_2CCH_3)_2.6H_2O$ and 340 mg of $Ga(NO_3)_3.6H_2O$. The pH was then brought to 8.5 with NaOH. The pale pink crystalline product was obtained via MeOH diffusion in the aqueous solution.

Preparation 12

Preparation of $K_4[MnGa_3(O)(OH)(O_2CCH_3)_2L_2]$

In a 50 ml Erlenmeyer flask, 268 mg of DHPTA was added to ~7 ml $H_2O$. The solution was brought to pH ~6 with KOH. Then 60 μl of 100% $CH_3COOH$ was added, followed by 100 mg of $Mn(O_2CCH_3)_2.6H_2O$ and 350 mg of $Ga(NO_3)_3.6H_2O$. The pH was brought to ~8 with KOH, the solution filtered and layered with MeOH to give pale pink crystalline product.

Preparation 13

Preparation of $Ba_2[(Ni_sMn_{1-s})Mn_3(O)(OH)(O_2CCH_3)_2L_2]$

In a 50 ml Erlenmeyer flask, 268 mg of DHPTA was added to ~8 ml $H_2O$. The pH was brought to ~6.5 with $Ba(OH_2).H_2O$. Next, 110 mg of $Ni(O_2CCH_3)_2.6H_2O$ and 330 mg of $Mn(O_2CCH_3)_2.6H_2O$ were added. The pH was brought to ~8 and then 1 ml $H_2O_2$ (30%) and 1 ml DMF were added slowly. The crystalline product was obtained by evaporation from the filtered solution.

Preparation 14

Preparation of $Ba_2[FeGa_3(O)(OH)(O_2CCH_3)_2L_2]$

In a 50 ml Erlenmeyer flask, 268 mg DHPTA was added to ~7 ml $H_2O$ containing 100 μl of 100% $CH_3COOH$ and the pH was brought to ~6.5 with $Ba(OH)_2.H_2O$. Then 454 mg of $Ga(NO_3)_2.6H_2O$ was added, pH was brought to 8 with $Ba(OH)_2.H_2O$, the solution filtered under argon and $Fe(O_2CCH_3)_2$ was added while stirring. Crystals formed via methanol diffusion.

Preparation 15

Preparation of $K_4[CoMn_3(O)(OH)(O_2CCH_3)_2L_2]$

In a 50 ml Erlenmeyer flask, 268 mg of DHPTA was added to ~10 ml $H_2O$ and the pH was brought to about 6.5 with KOH. Then 110 mg of $Co(O_2CCH_3)_2.4H_2O$ and 320 mg of $Mn(O_2CCH_3)_2.6H_2O$ was added to the solution. The pH was brought to ~8 with KOH and ~2 ml of 30% $H_2O_2$ was added dropwise giving a dark red-brown solution. Then 2 ml of DMF was added and the solution was filtered. Crystals were obtained by evaporation.

Preparation 16

Preparation of $Ca_2[Fe_4(O)(OH)(O_2CCH_3)_2L_2]$

In a 50 ml Erlenmeyer flask, 268 mg of DHPTA was added to ~8 ml $H_2O$ and the pH was adjusted to ~7.5 with $Ca(OH)_2$. Then 420 mg of $Fe(O_2CCH_3)_2$ was added. Then 1 ml of ~30% $H_2O_2$ was added giving a dark green solution. The pH was readjusted to 8.0 with $Ca(OH)_2$. Following the addition of 1 ml DMF, the sollution was filtered and crystallized by evaporation.

Examples 1 to 5

Figure 2:
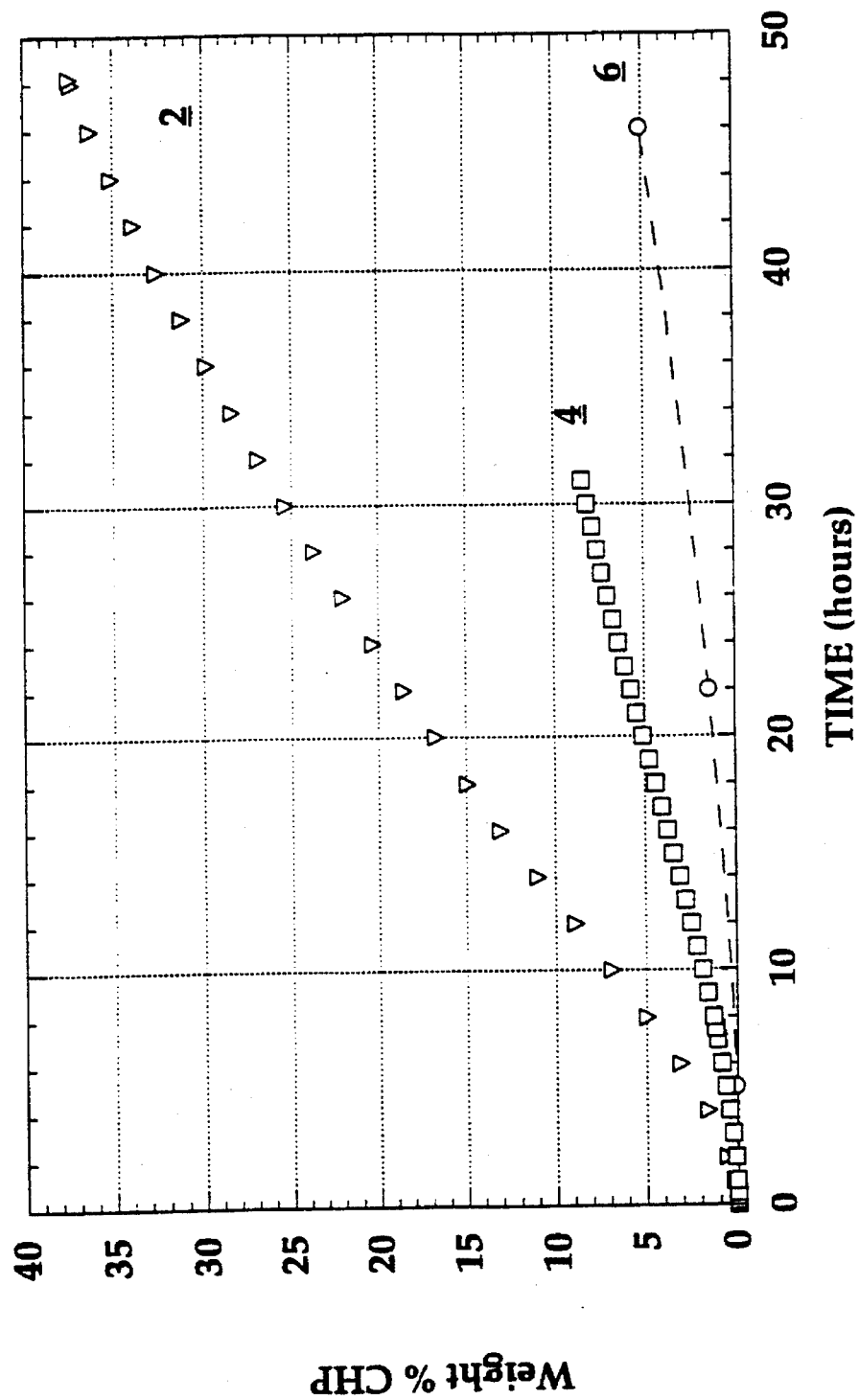

A series of runs were conducted using as catalysts the compounds listed in the Table below. In each example, 0.1 g of solid catalyst was added to 50 g of neat cumene in a flask. Air at 1 atm of pressure, was bubbled through the reaction mixture at a rate of 30 ml/min. The temperature of the reaction is maintained at 65° C. The conversion of cumene to cumene hydroperoxide (CHP) was monitored by iodometric titrations and oxygen uptake. The accompanying FIGS. 1 and 2 show the weight % CHP produced vs. time for various catalysts labeled as in Table. In FIG. 2, line 6 corresponds to the uncatalyzed auto-oxidation of cumene described in Comparative Example 1.

TABLE

| | $M_z[M_a(M_b)_3(O)(OH)(O_2CCH_3)_2L_2]$ | | |
|---|---|---|---|
| Example | M | $M_a$ | $M_b$ |
| 1 | Ba | $Ni_sMn_{1-s}$ | Mn |
| 2 | K | Mn | Ga |
| 3 | Na | Zn | Ga |
| 4 | Ba | Cu | Fe |
| 5 | Ba | Fe | Ga |

Comparative Example 1

12.0 grams of cumene (0.1 mole) was combined with 0.2 $cm^3$ of cumene hydroperoxide (as an initiator) and heated to 100° C. in a oxygen atmosphere with vigorous stirring. In three hours about 3% oxidation to cumene hydroperoxide occurs. Thus the rate observed for the CHP auto catalyzed oxidation at 100° C. is about 1% per hour. To compare this with an oxidation carried out at 65° C. a simple extrapolation can be done using the Arrhenius equation. Such as extrapolation indicates a reaction rate of about 0.1% per hour at 65° C. which is one order of magnitude smaller than that obtained with the catalysts of this invention.

What is claimed is:

1. A method for oxidizing an aryl alkyl hydrocarbon to an organic hydroperoxide comprising:

contacting an aryl alkyl hydrocarbon having a benzylic hydrogen with an oxygen containing gas and a catalytically effective amount of an oxo(hydroxo) bridged tetranuclear metal complex having a mixed metal core, one metal of the core being a divalent metal selected from Zn, Cu, Fe, Co, Ni, Mn or mixtures thereof and another metal being a trivalent metal selected from In, Fe, Mn, Ga and Al or mixtures thereof.

2. The method of claim 1 wherein the tetranuclear metal complex has the formula:

$$M_z[M_a(M_b)_3(O)_x(OH)_y(O_2CR)_2L_2]$$

wherein L is a ligand having the formula:

$$\begin{array}{c} -OOC-CH_2 \\ \phantom{-OOC-}\diagdown \\ \phantom{-OOC-CH_2}NCH_2 \\ \phantom{-OOC-}\diagup \\ -OOC-CH_2 \end{array} \begin{array}{c} O^- \\ | \\ -C-CH_2N \\ | \\ H \end{array} \begin{array}{c} CH_2-COO- \\ \diagup \\ \phantom{CH_2-}\diagdown \\ CH_2-COO- \end{array}$$

M is ammonium, an alkali metal ion or an alkaline earth metal ion, z is 4 when M is ammonium or an alkali metal ion and 2 when M is an alkaline earth metal ion $M_a$ is a divalent metal or mixture thereof, $M_b$ is a trivalent metal or mixture thereof, the contacting being for a time and at a temperature sufficient to form an organic hydroperoxide.

3. The method of claim 2 wherein the aryl alkyl hydrocarbon has the general formula:

$$\begin{array}{c} R_2 \\ | \\ R_1-C-H \\ | \\ Ar \end{array}$$

when $R_1$ and $R_2$ are independently hydrogen or organo groups and Ar is an aromatic group.

4. The method of claim 3 wherein the organo groups are alkyl groups of from 1 to about 10 carbon atoms.

5. The method of claim 4 wherein the oxygen-containing gas is air.

6. The method of claim 5 wherein the temperature is in the range of from about 0° C. to about 90° C.

7. The method of claim 6 wherein the aryl alkyl hydrocarbon is a liquid at the temperature range.

8. The method of claim 7 wherein the aryl alkyl hydrocarbon is dissolved in an inert solvent.

* * * * *